United States Patent
Rajagopal et al.

(10) Patent No.: US 10,376,892 B2
(45) Date of Patent: Aug. 13, 2019

(54) PC BOARD FLUIDIC DEVICES

(71) Applicant: CALIFORNIA INSTITUTE OF TECHNOLOGY, Pasadena, CA (US)

(72) Inventors: Aditya Rajagopal, Irvine, CA (US); Samson Chen, Flushing, NY (US); Axel Scherer, Barnard, VT (US); Christopher I. Walker, Palo Alto, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 207 days.

(21) Appl. No.: 15/360,691

(22) Filed: Nov. 23, 2016

(65) Prior Publication Data

US 2017/0072399 A1    Mar. 16, 2017

Related U.S. Application Data

(62) Division of application No. 13/763,352, filed on Feb. 8, 2013, now Pat. No. 9,533,308.

(60) Provisional application No. 61/597,554, filed on Feb. 10, 2012.

(51) Int. Cl.
| | |
|---|---|
| *C12Q 1/68* | (2018.01) |
| *B01L 7/00* | (2006.01) |
| *H05K 3/46* | (2006.01) |
| *B01L 3/00* | (2006.01) |
| *H05K 1/02* | (2006.01) |
| *C12Q 1/686* | (2018.01) |

(52) U.S. Cl.
CPC ............ *B01L 7/52* (2013.01); *B01L 3/502707* (2013.01); *C12Q 1/686* (2013.01); *H05K 1/028* (2013.01); *H05K 1/0212* (2013.01); *H05K 1/0272* (2013.01); *H05K 3/46* (2013.01); *B01L 2200/147* (2013.01); *B01L 2300/0816* (2013.01); *B01L 2300/0893* (2013.01); *B01L 2300/12* (2013.01); *B01L 2300/123* (2013.01); *B01L 2300/1827* (2013.01); *B01L 2300/1844* (2013.01); *H05K 3/4697* (2013.01); *Y10T 29/49124* (2015.01)

(58) Field of Classification Search
None
See application file for complete search history.

(56) References Cited

U.S. PATENT DOCUMENTS

| | | |
|---|---|---|
| 3,945,618 A | 3/1976 | Shoh |
| 6,379,974 B1 | 4/2002 | Parce et al. |
| 6,443,179 B1 | 9/2002 | Benavides et al. |
| 6,572,830 B1 | 6/2003 | Burdon et al. |
| 6,589,779 B1 | 7/2003 | McDevitt et al. |
| 6,590,032 B2 | 7/2003 | Furukawa et al. |

(Continued)

OTHER PUBLICATIONS

Lee et al. (IEEE Sensors Journal, 2008, vol. 8, No. 5, p. 558-564) (Year: 2008).*

(Continued)

*Primary Examiner* — Stephanie K Mummert
(74) *Attorney, Agent, or Firm* — Steinfl + Bruno, LLP

(57) ABSTRACT

PC board fluidic devices for performing a Polymerase Chain Reaction (PCR) are disclosed. The devices comprise a printed circuit board and a PCR chamber. The PCR chamber is a fluidic chamber and is located in, or is part of, the PC board. The PC board can include a coil trace heating element with a temperature sensor and controller.

14 Claims, 13 Drawing Sheets

(56) References Cited

U.S. PATENT DOCUMENTS

| | | | |
|---|---|---|---|
| 6,706,519 | B1 | 3/2004 | Kellogg et al. |
| 7,682,819 | B2 | 3/2010 | Sarofim et al. |
| 8,414,785 | B2 | 4/2013 | Walker et al. |
| 9,533,308 | B2 * | 1/2017 | Rajagopal ......... B01L 3/502707 |
| 2002/0127152 | A1 | 9/2002 | Benett et al. |
| 2002/0168299 | A1 | 11/2002 | Chang et al. |
| 2003/0064507 | A1 | 4/2003 | Gallagher et al. |
| 2004/0027915 | A1 | 2/2004 | Lowe et al. |
| 2004/0067603 | A1 | 4/2004 | Hagen |
| 2005/0009101 | A1 | 1/2005 | Blackburn |
| 2005/0158725 | A1 | 7/2005 | Yukimasa et al. |
| 2007/0026426 | A1 | 2/2007 | Fuernkranz et al. |
| 2007/0047377 | A1 | 3/2007 | Bang et al. |
| 2007/0093045 | A1 | 4/2007 | Yamaguchi et al. |
| 2007/0154922 | A1 | 7/2007 | Collier et al. |
| 2007/0196237 | A1 | 8/2007 | Neuzil et al. |
| 2008/0038163 | A1 * | 2/2008 | Boege ....................... B01L 7/52 422/600 |
| 2008/0160601 | A1 | 7/2008 | Handique |
| 2009/0291507 | A1 | 11/2009 | Clemmens et al. |
| 2010/0084371 | A1 | 4/2010 | Walker et al. |
| 2010/0221726 | A1 | 9/2010 | Zenhausern et al. |
| 2012/0264202 | A1 | 10/2012 | Walker et al. |
| 2013/0210080 | A1 | 8/2013 | Rajagopal et al. |

OTHER PUBLICATIONS

Non-Final Office Action for U.S. Appl. No. 12/572,211, filed Oct. 1, 2009 on behalf of Christopher I. Walker, dated May 8, 2012.
Final Office Action for U.S. Appl. No. 12/572,211, filed Oct. 1, 2009 on behalf of Christopher I. Walker, dated Oct. 10, 2012.
Notice of Allowance for U.S. Appl. No. 12/572,211, filed Oct. 1, 2009 on behalf of Christopher I. Walker, dated Jan. 11, 2013.
Duffy, D., et al., Rapid prototyping of microfluidic systems in poly(dimethylsiloxane), Analytical Chemistry 1998, 70: 4974-4984.
Laritz, C., et al., A microfluidic pH-regulation system based on printed circuit board technology, Sensors and Actuators 2000, 84: 230-235.
Lian, K., et al., Integrated microfluidic components on a printed wiring board platform, Sensors and Actuators B: Chemical 2009, 138: 21-27.
Merkel, T., et al., A new technology for fluidic microsystems based on PCB technology, Sensors and Actuators 1999, 77: 98-105.
Metz, S., et al., Polyimide-based microfluidic devices, Lab on a Chip 2001, 1: 29-34.
Unger, M., et al., Monolithic microfabricated valves and pumps by multilayer soft lithography, Science 2000, 288: 113-116.
Wego, A., et al., Fluidic microsystems based on printed circuit board technology, Journal of Micromechanical and Microengineering 2001, 11: 528-531.
Extended European Search Report dated Aug. 1, 2014 for EP Application No. 12760549 filed Mar. 19, 2012 in the name of California Institute of Technology, 6 pgs.
European Communication pursuant to Rules 70(2) and 70a(2) EPC dated Aug. 20, 2014 for EP Application No. 12760549 filed Mar. 19, 2012 in the name of California Institute of Technology, 1 pg.
PCT International Search Report dated Nov. 1, 2012 for PCT Application No. PCT/US2012/029631 filed on Mar. 19, 2012 in the name of California Institute of Technology et al., 4 pgs.
PCT Written Opinion dated Nov. 1, 2012 for PCT Application No. PCT/US2012/029631 filed on Mar. 19, 2012 in the name of California Institute of Technology et al., 5 pgs.

* cited by examiner

PC BOARD FLUIDIC DEVICES

CROSS REFERENCE TO RELATED APPLICATIONS

The present application is a Divisional of U.S. application Ser. No. 13/763,352 filed on Feb. 8, 2013, which, in turn, claims priority to U.S. provisional application 61/597,554 for "PC Board-based Polymerase Chain Reaction System, Methods and Materials" filed on Feb. 10, 2012, both of which are herein incorporated by reference in their entirety.

FIELD

The present disclosure relates to PC board fluidic devices, such apparatuses for performing a Polymerase Chain Reaction (PCR), methods for manufacturing apparatuses for performing a Polymerase Chain Reaction (PCR) and methods for performing a Polymerase Chain Reaction (PCR).

BACKGROUND

Polymerase chain reaction (PCR) is one of the cornerstones of modern biology, as it permits for the amplification of specific sequences of DNA from naturally occurring concentrations to concentrations detectable by other molecular biology techniques. In addition to the widespread use of polymerase chain reaction (PCR) as a technique in laboratories, it is also extensively used in medicine as a gold standard for the detection of infectious pathogens.

SUMMARY

According to a first aspect of the present disclosure, an apparatus for performing a Polymerase Chain Reaction (PCR) is provided, the apparatus comprising a PCR chamber for performing a Polymerase Chain Reaction and a printed circuit board (PCB) fluidic device, wherein the PCR chamber is a fluidic chamber and is located in, or is part of, the printed circuit board (PCB) fluidic device.

According to a second aspect of the present disclosure, a method for manufacturing an apparatus for performing Polymerase Chain Reaction (PCR) is provided, the method including the step of manufacturing the apparatus for performing PCR using a printed circuit board (PCB) fluidics fabrication process.

According to a third aspect of the disclosure, a method for performing a Polymerase Chain Reaction (PCR) is provided, the method comprising performing a PCR in a PCR chamber, wherein the PCR chamber is a fluidic chamber part of a printed circuit board (PCB) fluidic device.

According to a fourth aspect of the disclosure, a printed circuit board (PCB) fluidic device is presented, the printed circuit board (PCB) fluidic device including a Polymerase Chain Reaction (PCR) chamber for performing a PCR.

Further aspects of the disclosure are shown in the specification, drawings and claims of the present application.

DETAILED DESCRIPTION

PCR is a fairly complex procedure to implement, which has limited its use in the context of point-of-care medicine. In fact, in PCR, a target DNA sequence is typically mixed with a DNA polymerase enzyme, DNA base pairs, DNA primers with base pairs corresponding to the beginning and end of the target DNA sequence, and a variety of other reagents to improve the performance of the procedure.

In addition to the complexity of the reagents involved, the actual execution of the procedure can require a sample to be thermally cycled among several different temperatures. These temperature steps typically can involve a denaturation step, where a double-stranded DNA molecule to be copied is split into two single-stranded DNA molecules (typically in the 94-96C range); an annealing step, where the DNA primers bind to the target sequence on the single-stranded DNA molecules (50-65C range); and an extension step, where the DNA polymerase enzyme makes a copy of the single stranded DNA molecules beginning from each DNA primer, producing double stranded DNA molecules and doubling the concentration of the target DNA sequence.

Current commercial systems for performing this thermal cycling, have typically been large, bulky benchtop devices which use expensive Peltier junction devices to quickly heat and cool samples.

Based on the above recognitions and observations of the inventors, with reference to the attached drawings and according to some embodiments of the present disclosure, a PCR system based on printed circuit board (PCB) fluidic device is disclosed.

Figure 1:
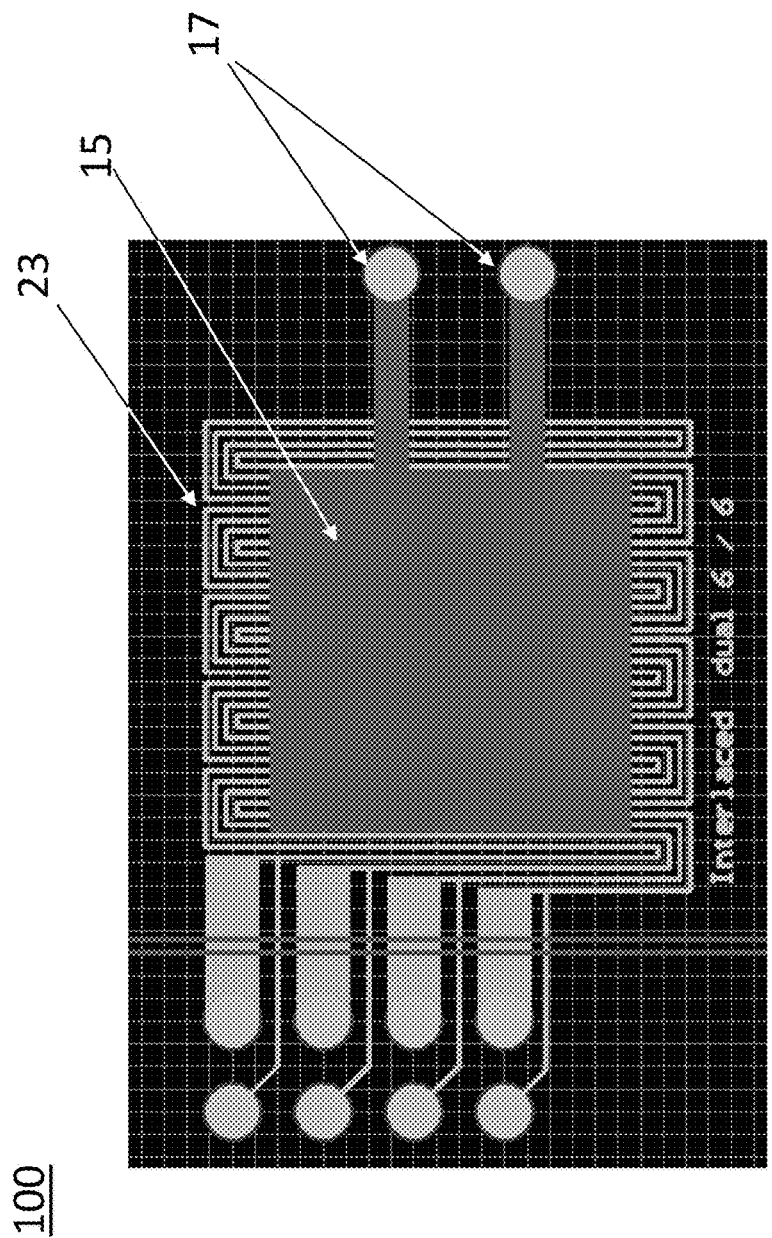
FIG. 1 shows a view of an apparatus layout according to some embodiments of the present disclosure, comprising a heater coil layer and a chamber layer.

According to some aspects of the present disclosure, FIG. 1 shows an apparatus for performing a Polymerase Chain Reaction (PCR) which can comprise a PCR chamber (15) for performing a Polymerase Chain Reaction placed in a printed circuit board (PCB) fluidic device (100). The PCR chamber is a fluidic chamber (15) and is located in, or is part of, the printed circuit board (PCB) fluidic device (100). It follows that the Polymerase Chain Reaction described here above can be performed in the printed circuit board (PCB) fluidic device (100). The term "printed circuit board (PCB) fluidic device (100)" can be meant as a chip structure provided with ports and channels suitable for passage of fluid. In particular, reactants of Polymerase Chain Reaction can be fed in fluidic channels and/or ports (17) of the printed circuit board (PCB) fluidic device (100) to react in the PCR chamber (15). It further follows that a PCR chamber is part of, or is embedded in, or is integrated with, the layers of a printed circuit board (PCB) fluidic device (100).

According to some aspects of the present disclosure, PCB fluidics can permit, for example, the integration of both fluidic and electronic systems on the same board with a few modifications to the standard PCB fabrication process.

Due to the current maturity of the PCB fabrication process and the ubiquity of PCBs, both per-unit manufacturing costs and one-time costs (tooling, NRE) can be exceptionally low, and turnaround time can be short. These factors can make the apparatus according of the present disclosure particularly attractive for integration into point-of-care pathogen identification systems which could permit patients, possibly even in the developing world, to very quickly find out whether or not they are infected with HIV, tuberculosis, or other pathogens.

Figure 3:
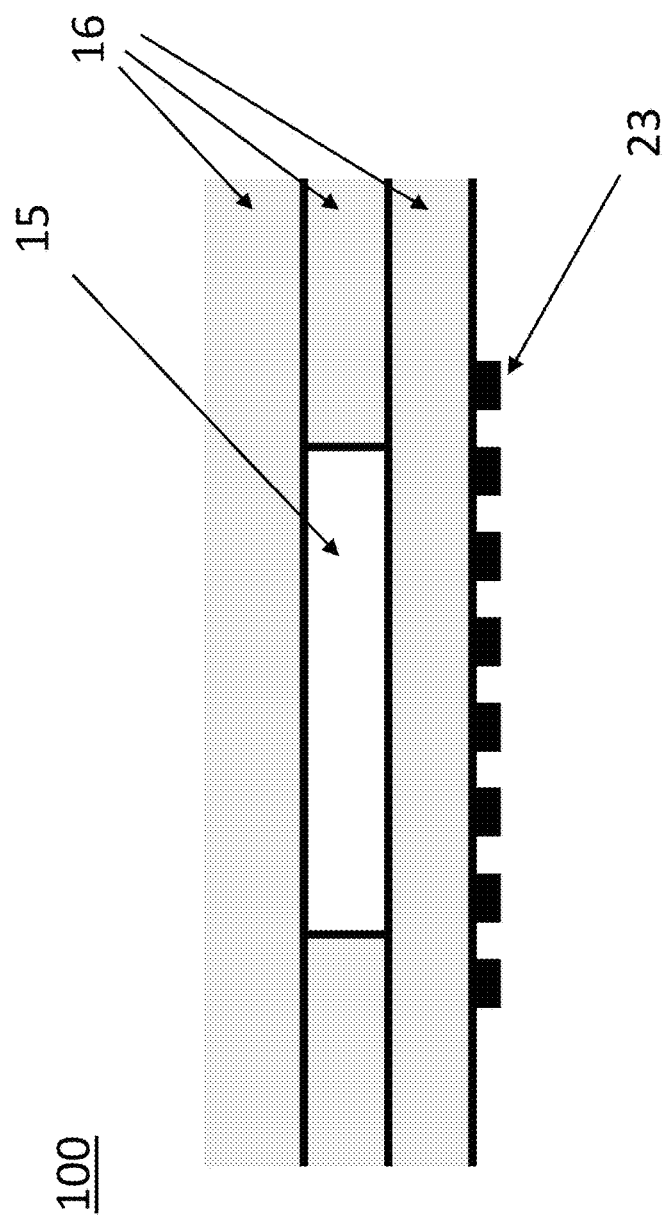
FIG. 3 shows a schematic cross sectional view of the apparatus of FIG. 1.

With reference to FIG. 1 and FIG. 3, according to some embodiments of the present disclosure, a PCR chamber (15) of dimensions appropriate for the required reaction (typically in the microliter range) can be formed using multilayer PCB fluidics fabrication methods.

The apparatus can include a multilayer flex-on-rigid backing design with flex layers (16), wherein the PCR chamber (15) can be contained within the flex layers (16). In some embodiments of the present disclosure the PCR chamber is contained entirely within the flex layers (16). The chamber can be etched out from the flex layers. It follows that, according to some embodiments of the present disclosure, the entire apparatus can be a multilayer flex-on-rigid backing design.

According to further aspects of the present disclosure, the apparatus can be composed of materials compatible with the PCR reaction. For example looking at FIG. 3, the flex layers (16) can be made of Kapton compatible with the polymerase chain reaction. The person skilled in the art will know that Kapton is a polyimide and as such has good thermal stability, good chemical resistance and excellent mechanical properties.

Figure 4:
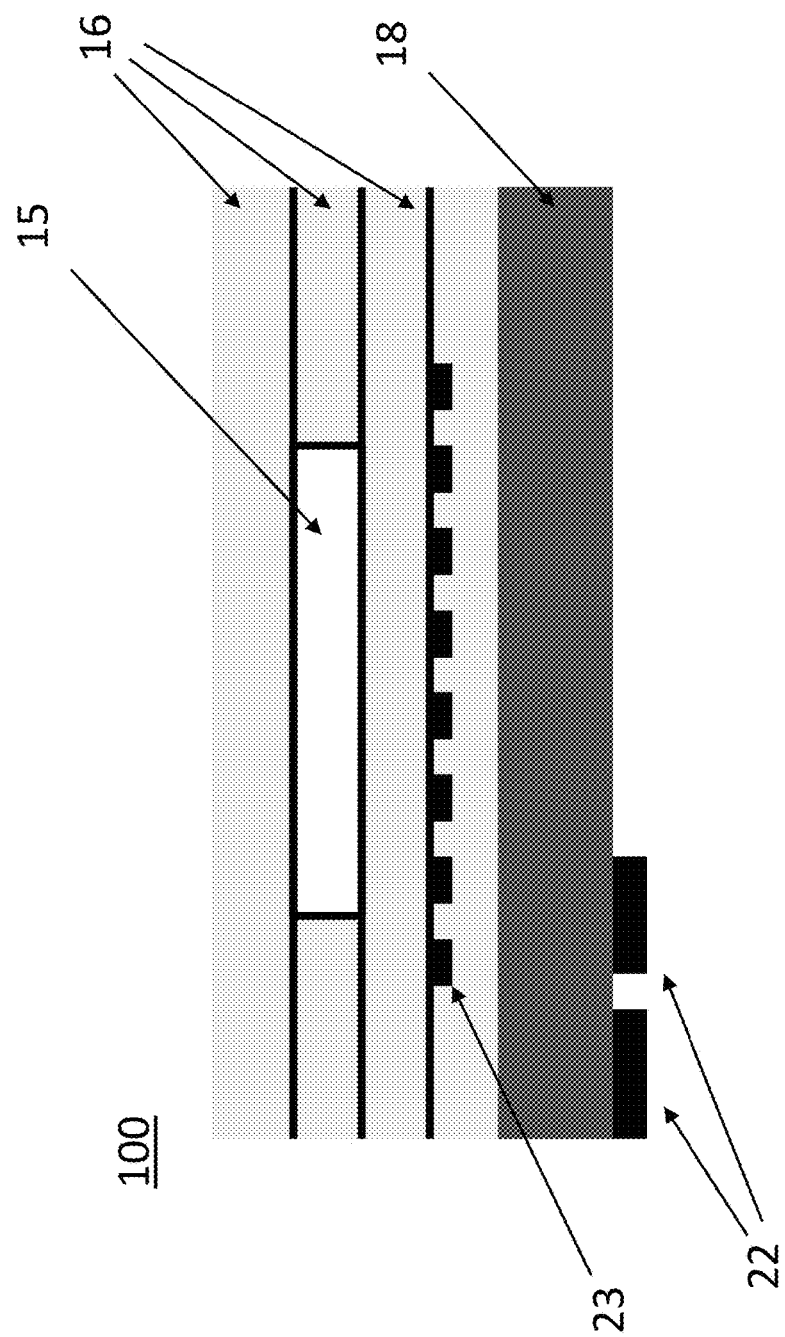
FIG. 4 shows a schematic cross sectional view of the apparatus of FIG. 1, wherein a rigid printed circuit board layer is added.
Figure 12:
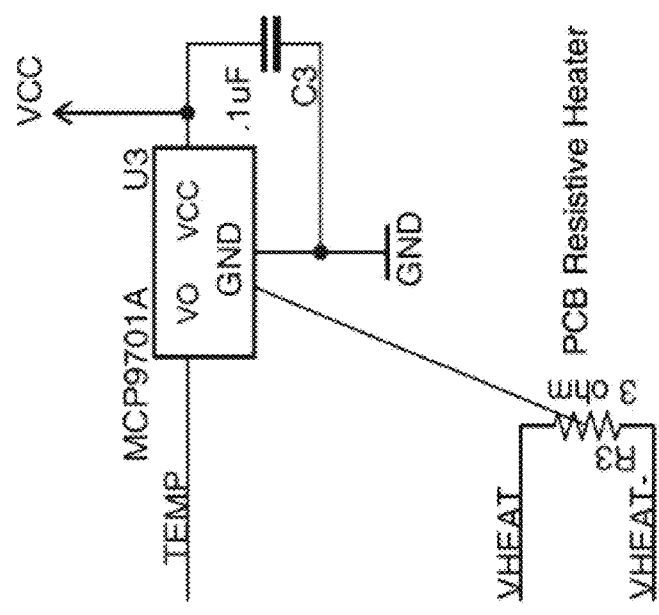
FIG. 12 shows a schematic diagram of a further part of a controller for an apparatus according to some embodiments of the present disclosure.
Figure 13:
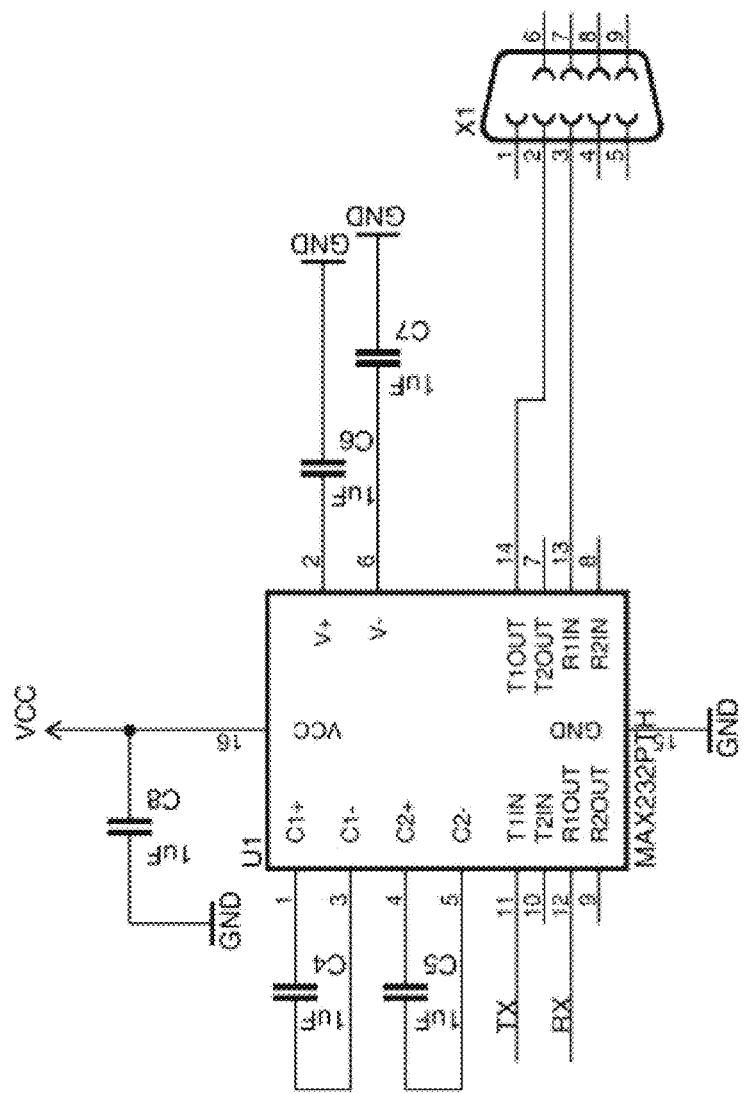
FIG. 13 shows a schematic diagram of a further part of a controller for an apparatus according to some embodiments of the present disclosure.

As shown in FIG. 4, a basement (18) can be further located beneath the flex layers (16), wherein the basement (18) may contain electronic circuit board traces (22) as well as some electronic devices as shown for example in FIG. 12. The basement can further contain a heater (23) for heating the PCR chamber. The basement can be a FR-4 based construction, which is a rigid fiberglass/composite sheet commonly used to fabricate rigid printed circuit boards. Although FR-4 material is not biocompatible with PCR, in this embodiment it is used in a layer that can be not in contact with the reagents which may adversely impact operation of electronic components included within the FR-4 layer. It follows that according to further aspects of the present disclosure, the printed circuit board (PCB) fluidic device (100) can be designed and configured to include both the PCR chamber and the traces and electronics device. In fact, the PCR chamber and the traces and electronics device can be located in different layers of the printed circuit board (PCB) fluidic device (100).

Figure 2:
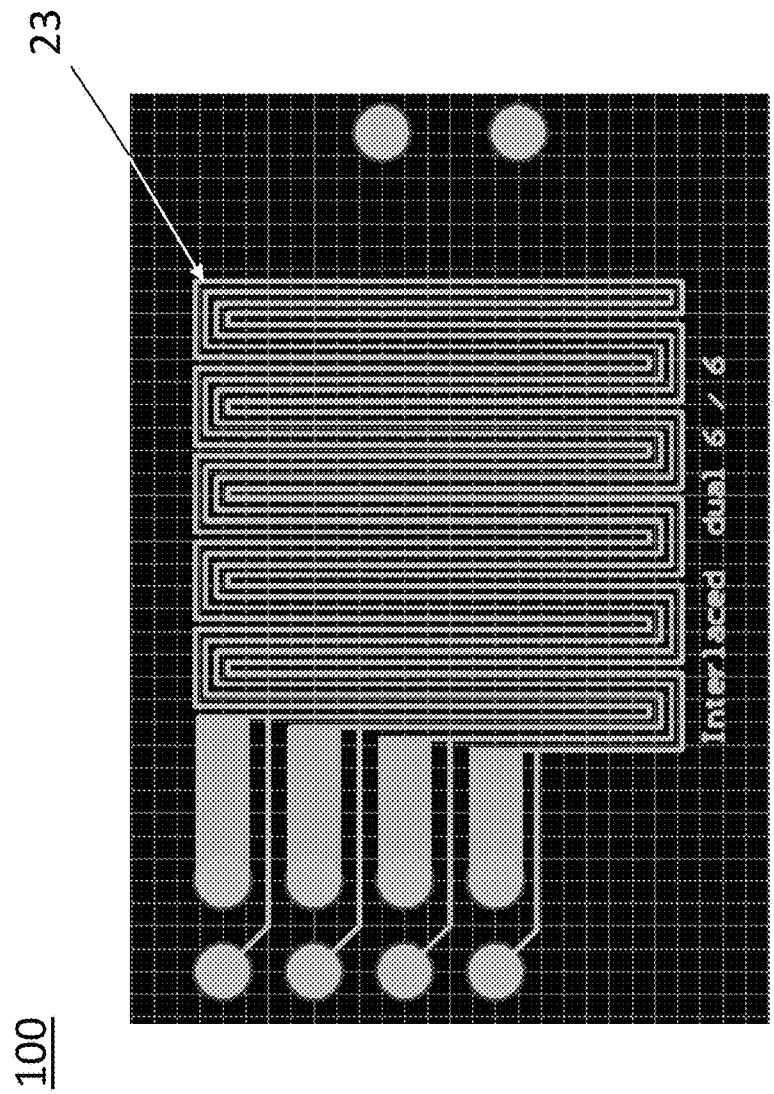
FIG. 2 shows the heater coil layer only of the apparatus of FIG. 1.

According to some aspects of the present disclosure, the heater (23) for heating the PCR chamber (15) can be a coil trace, for example a copper coil trace, located beneath the PCR chamber for heating reactants of the polymerase chain reaction. As it shown in FIG. 3, the coil trace can be indirectly connected, without any direct connection, to the chamber (15). More in particular and as shown in FIG. 1 and FIG. 2, the coil trace can be a long, thin coil trace beneath the PCR chamber (15) for heating the sample via controlled current flow within the coil. The coil trace may be etched within a flex layer underneath the chamber, as depicted in FIG. 3, or alternatively, it may be etched within a rigid FR-4 layer and also placed underneath the chamber. As a consequence, the chip substrate may be all polyimide or a hybrid polyimide/FR-4.

Figure 7:
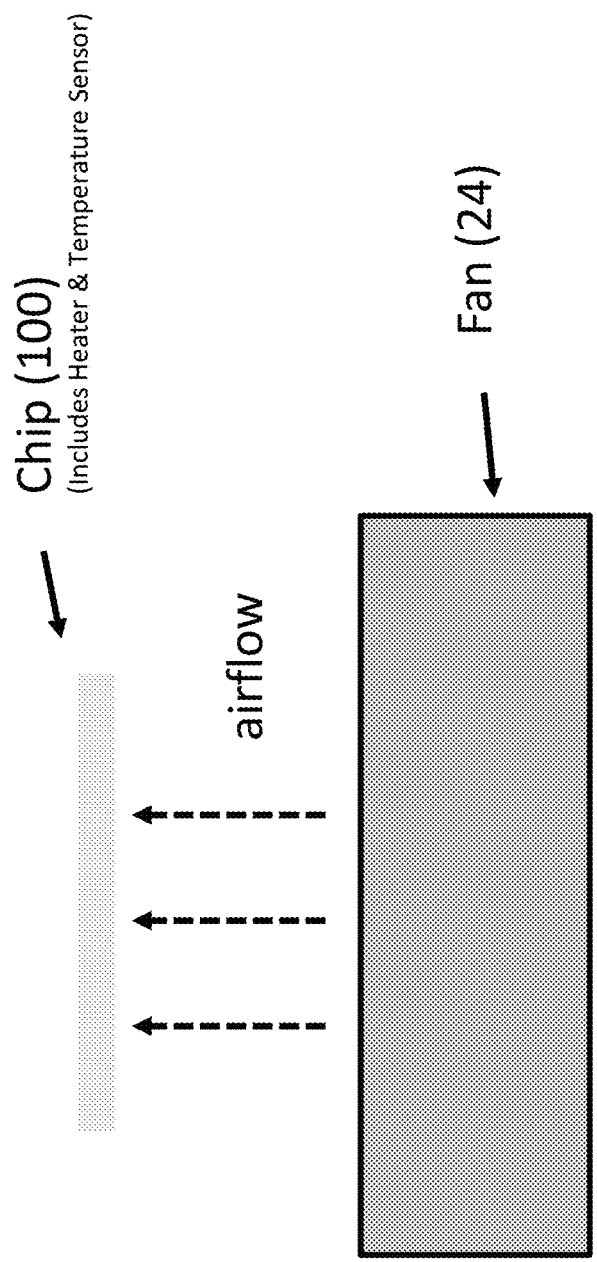
FIG. 7 shows an exemplary cooling method for a chamber according to some embodiments of the present disclosure.

According to some embodiments of the present disclosure a cooler (e.g. fan (24) in FIG. 7) can be provided to cool down the chamber when required. In particular, cooling can be accomplished either passively (e.g. stopping the heating process), or actively, for example with forced convection through a fan (24), as all of the temperatures required for PCR can be above room temperature. As shown in FIG. 7, the cooler (24) for cooling the PCR chamber can be a structurally separated device with respect to the heater (23). In the exemplary embodiment of FIG. 8, the cooler can be a small fan placed within a metal enclosure underneath the sample polyimide chip. In other embodiments, the cooler may be placed elsewhere with respect to the sample polyimide chip, but in close proximity to the latter, as to provide efficient cooling by forcing air onto the sample polyimide chip. For the particular noted case where the coil is on an FR-4 layer, cooling from underneath is not possible as the FR-4 material is an excellent insulator. In this case, the fan may be placed above the sample polyimide and forcing air through the top of the sample. Alternatively, the embodiment of FIG. 8 may be used in the case where the coil is on an FR-4 based layer provided a cutout is made in the FR-4 in the region of the chamber and the heating coil. It should be further noted that the cooler and the heater are opportunely used to set temperatures suitable for the PCR reaction cycle. The temperatures can be higher than room temperatures.

Figure 5:
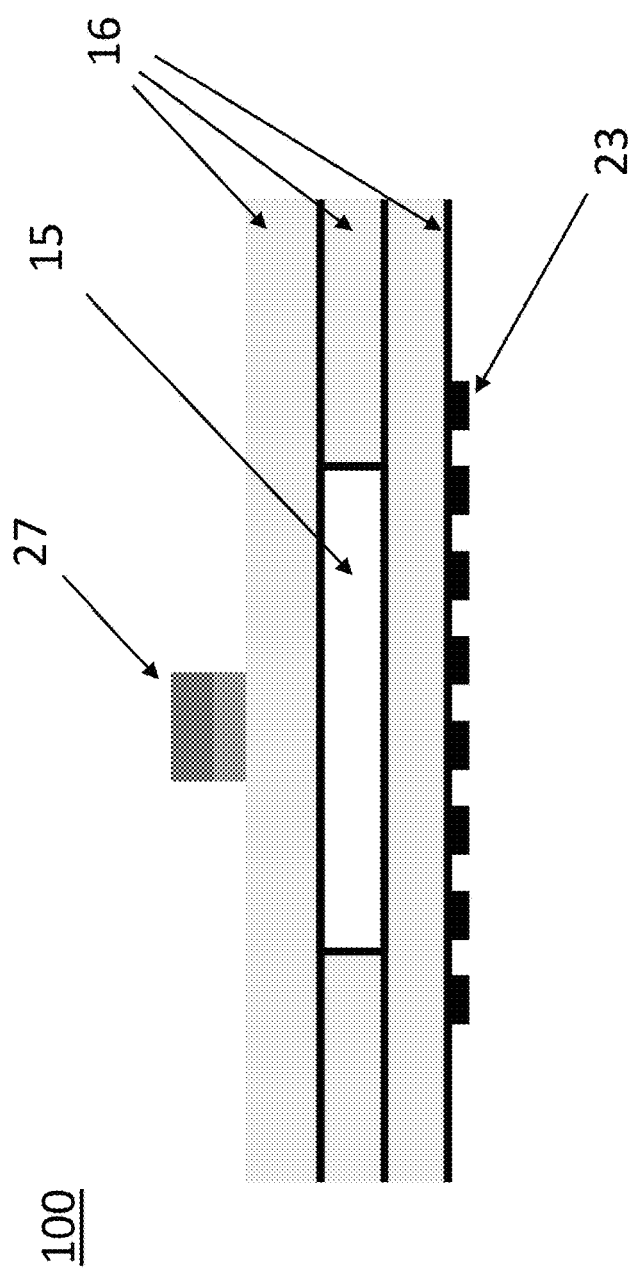
FIG. 5 shows a schematic cross sectional view of an apparatus according to some embodiments of the present disclosure, wherein a temperature sensor is bonded on top of the chamber layer.
Figure 6:
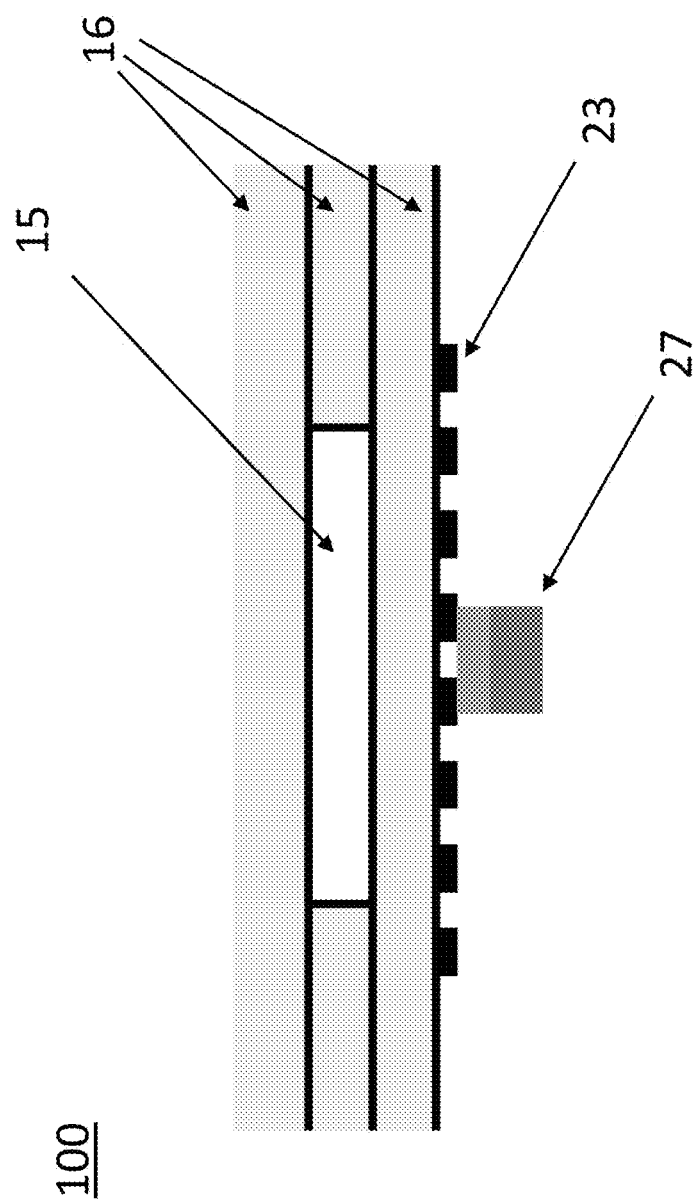
FIG. 6 shows a schematic cross sectional view of an apparatus according to some embodiments of the present disclosure, wherein a temperature sensor is bonded on the bottom of the chamber layer.
Figure 8:
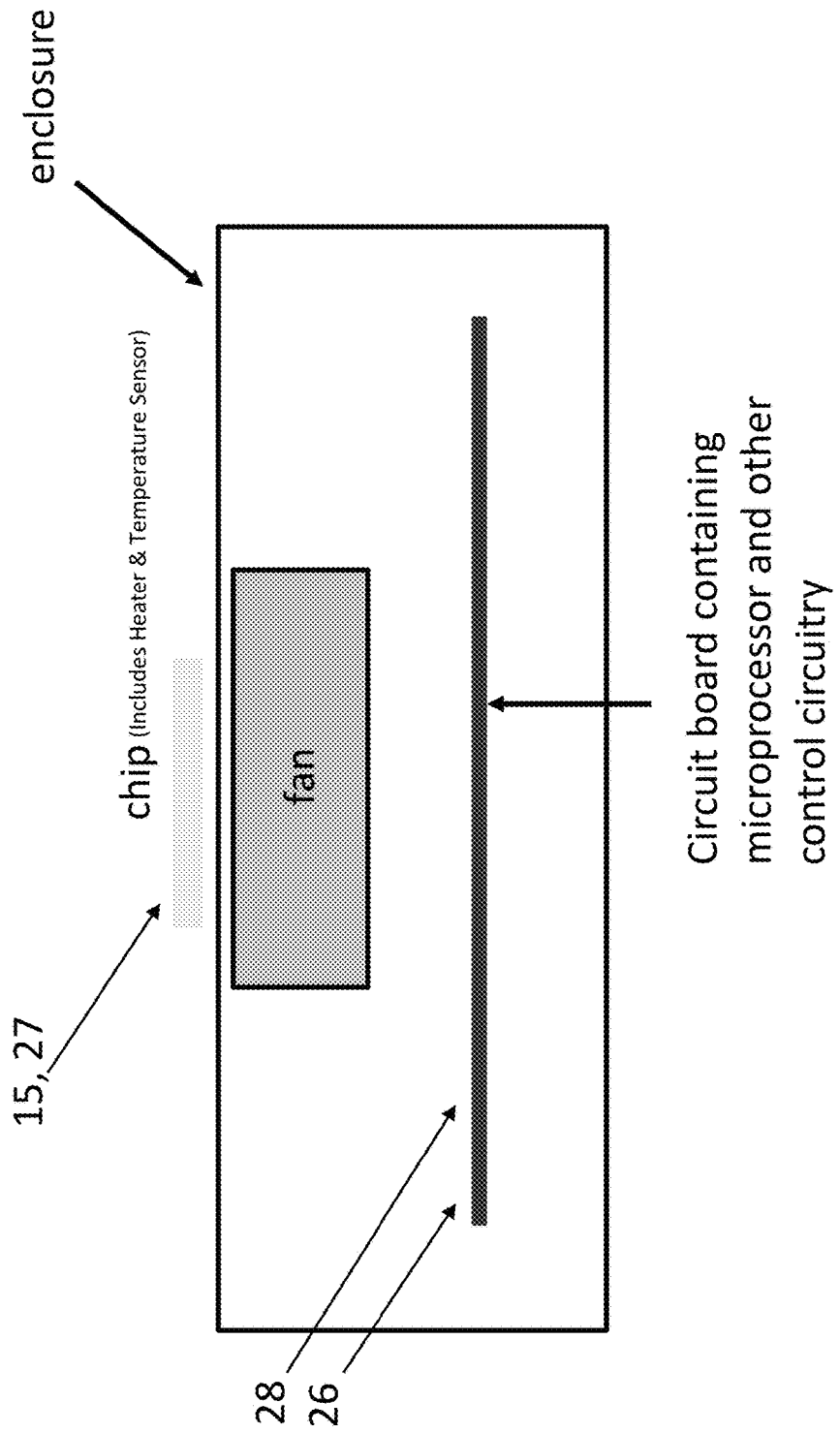
FIG. 8 shows an exemplary diagram of a printed circuit board (PCB) based Polymerase Chain Reaction System according to some embodiments of the present disclosure.
Figure 11:
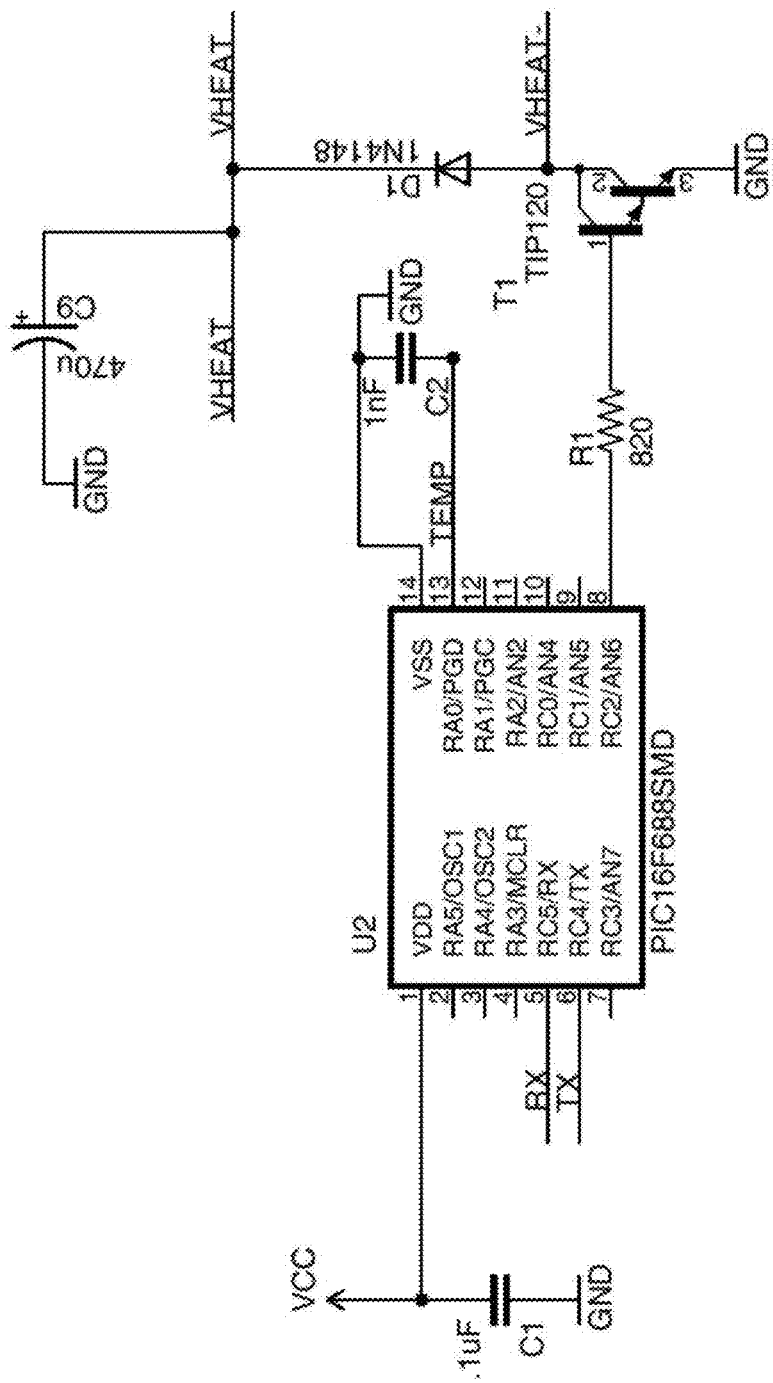
FIG. 11 shows a schematic diagram of a part of a controller for an apparatus according to some embodiments of the present disclosure.

In addition, according to further aspects of the present disclosure and as depicted by FIGS. 8, 11 and 12, a PCR temperature controller (26) having a temperature sensing device (27) can be provided. The PCR temperature controller (26) can be associated to the PCR chamber (15) for sensing and controlling the temperature in the PCR chamber. Temperature sensing may be performed using a multitude of methods. For example, the temperature sensing device can include a temperature sensor bonded directly, or located, onto the bottom of the PCR chamber as depicted by FIG. 6, or alternatively the temperature sensor can be bonded directly, or located, onto a top portion of the PCR chamber (15) as depicted by FIG. 5. The temperature sensor used may be for example an MCP9701 low-power linear active thermistor manufactured by Microchip, and which provides an output voltage range of 500 mV at a 10 mV/C resolution. It follows that the temperature sensing device (27) can be included within the circuit board (PCB) fluidic device (100).

According to alternative embodiments of the present disclosure a sensitive resistance measurement circuit can be applied. The sensitive resistance measurement circuit can use the temperature coefficient of resistivity (TCR) of the copper coil (which forms the heater) beneath the PCR chamber to measure the chamber temperature.

Because of the complexity of a control scheme, a microprocessor can be useful for a PCR temperature controller. It follows that according to further aspects of the present disclosure, the PCR temperature controller includes a microprocessor. FIG. 11 shows a portion of the control circuitry wherein a microprocessor (U2) is used to implement the temperature controller. In particular, pin 8 of U2 is used to control a current through the heater coil via a Darlington transistor (T1) which has high current capability, which current in turn causes heat dissipation through the coil underneath the chamber. A temperature sensor at the vicinity of the chamber (FIGS. 5, 6) detects the temperature and provides the microprocessor (U2) with a voltage proportional to the sensed temperature at pin 13 of U2.

Figure 9:
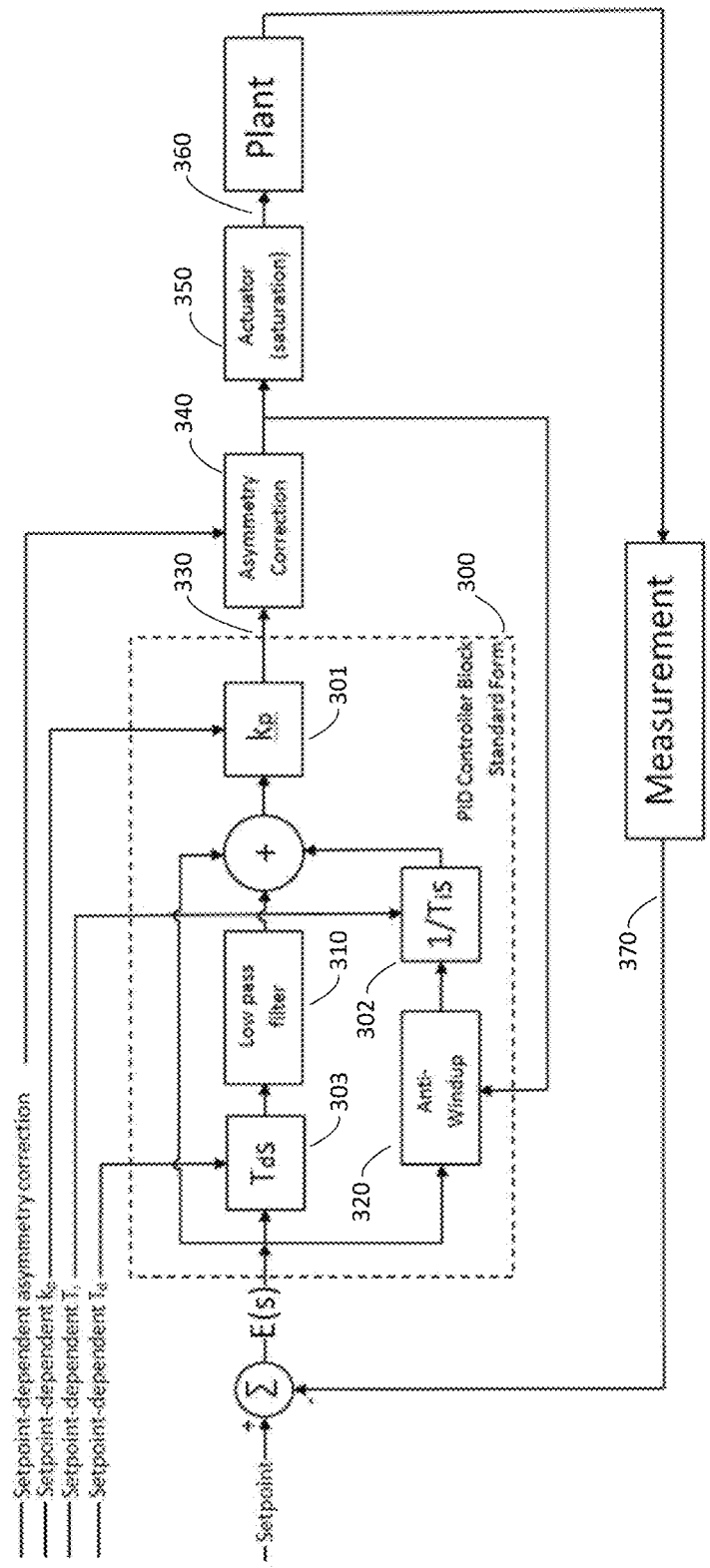
FIG. 9 shows a block diagram of a controller for an apparatus according to some embodiments of the present disclosure.
Figure 10:
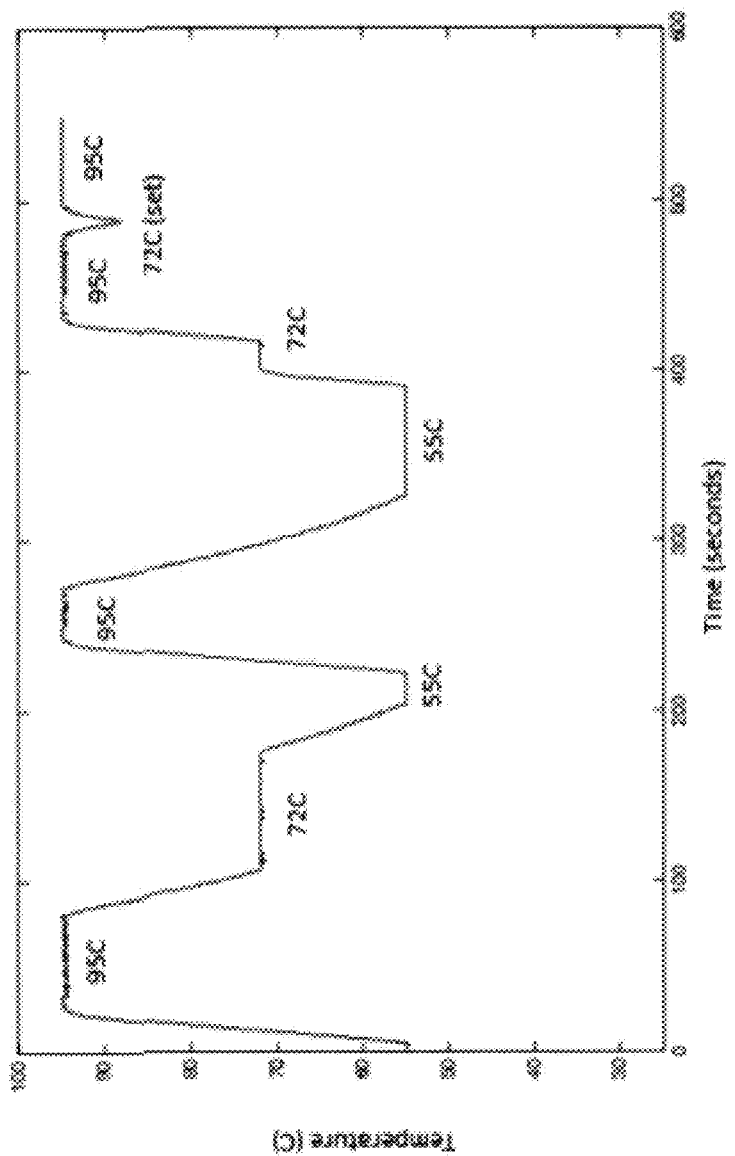
FIG. 10 shows preliminary heating and cooling curves for a controller of an apparatus according to some embodiments of the present disclosure.

With reference to FIG. 9 and FIG. 10, according to one embodiment of the present disclosure, the design, both in terms of hardware and software, can be optimized for the lowest possible cost. In particular, FIG. 10 shows that the performance of a preliminary version of the controller, particularly for PCR-critical temperatures, can be sufficient for PCR. In terms of software, a fixed-point PID controller can be implemented to reduce processing power necessary in the microcontroller (e.g. as used in current commercial systems), permitting the use of an extremely low cost Microchip PICI6F/PICI2F series 8-bit microcontroller, which is shown in FIG. 11 (U2). This particular fixed point controller can employ several components not common to most PID controllers (as it is shown in FIG. 9) to improve performance without requiring excessive processing power and associated high cost.

Nonlinearity correction, actuator asymmetry correction, anti-windup, and low pass filter are all additional features in the controller not present in canonical PID controller, all of which improve control performance with limited computational resources.

The optimized PID controller shown in FIG. 9 is used to control the temperature of the chamber by minimizing the temperature error E(s) derived from the difference between the desired temperature, provided by the Setpoint control input to the PID controller, and the measured temperature (370) obtained by the Measurement device. The skilled person may appreciate the added features in the controller of FIG. 9 with respect to a standard (canonical) PID controller which are now described in further details. Going back to FIG. 9, the temperature error E(s) is fed to a modified PID Controller Block (300) comprising the three standard processing units of a PID controller, the proportional unit (301) represented by a constant $K_p$ function, the integral unit (302) represented by $1/T_i s$ function and the derivative unit (303) represented by $T_d s$ function, where the constants $K_p$, $T_i$ and $T_d$ are programmed values dependent on the input Setpoint. Each of these units provides a correction term based on the temperature error E(s).

In the embodiment of FIG. 9, correction term from the differential unit is subjected to a low pass filter (310), thus controlling the rate of change which may be dictated by a relatively large swing in the error component, either by virtue of the limited resolution of the controller or the requested Setpoint. Similarly, an Anti-Windup component (320) is provided prior to feeding the error E(s) to the derivative unit (302), thus countering excessive overshoot of the controller in response to large swings in Setpoint that may be requested by the process. The evaluated correction terms by each of the units are then summed to create a combined correction (330) out of the PID Controller Block (300). In order to adjust for further process limitations, additional conditioning to the combined correction (330) is performed. In particular, in order to compensate for difference in process response between ramping up (heating) and ramping down (cooling) the temperature, an Asymmetry correction unit (340), which function is dependent of the Setpoint, is added to the controller.

Finally, in order to compensate for the non-linear response of the actuator when driven at high gains (e.g. close to saturation), an Actuator-saturation correction unit (350) is provided. The person skilled in the art will appreciate the added performance obtained by these features and as evaluated by the heating/cooling curve of FIG. 10. It should be further noted that the results depicted by FIG. 10 are obtained by using forced-air cooling and resistive heating (coil). The integrated heater on the PCB fluidic device (100) is connected to the lines marked "VHEAT" and "VHEAT-" of FIG. 11. When the Darlington transistor (T1) is turned on, the heater element is connected to ground via the transistor, thus causing current to flow from "VHEAT" power terminal to ground through the heater (effectively the transistor controlling the current flow though the coil).

According to further aspects of the present disclosure, when active cooling is used, the temperature dynamics of the chip can differ depending on whether it is being cooled (or heated). A simple model of heating/cooling can be Newton's law of cooling, which states that heat transfer can be proportional to the difference in temperature. In other words, the control dynamics of a purely passively cooled system are identical under heating and cooling. From a control loop viewpoint, this can be a simple pole, at same location, for both passive cooling and heating. When active cooling is used, e.g. forced air from a fan, the proportionality constantly changes. This affects the location of the pole. When forced air is used when the chip is being cooled, but not heated, the control loop must account for this asymmetry. Since it can be known whether the printed circuit board (PCB) fluidic device (100) is under a heating phase or under a cooling phase, an asymmetry correction into the control system can be designed.

In addition it should be noted that, according to some aspects of the present disclosure, the use of software decimation techniques additionally permits increased resolution without increased circuit complexity and/or temperature sensor and other hardware cost.

It should be further noted that, according to some aspects of the present disclosure, because of the use of separate heating (copper heater) and cooling (fan) devices, usage of an H-bridge, which requires four high power transistors and more complex driver circuitry, can be avoided. Instead, only two fairly low cost transistors may be used, one to drive the heater and one to drive the cooler.

It further follows that the apparatus according to the present disclosure can also implement a cost-optimized design for temperature control. Therefore, it appears that the apparatus of some embodiments of the present disclosure can be superior to conventional devices in terms of cost and complexity and with similar thermal performance.

The examples set forth above are provided to give those of ordinary skill in the art a complete disclosure and description of how to make and use the embodiments of the disclosure, and are not intended to limit the scope of what the inventors regard as their disclosure. Modifications of the above-described modes for carrying out the disclosure, including pressure control devices, accumulators, and so forth, may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A printed circuit board (PCB), comprising:
   a Polymerase Chain Reaction (PCR) chamber for performing a PCR;
   a printed circuit board (PCB) fluidic device,
   wherein the PCR chamber is a fluidic chamber and is located in the printed circuit board (PCB) fluidic device.

2. The printed circuit board (PCB) of claim 1, wherein the printed circuit board (PCB) fluidic device includes a multi-layer flex-on-rigid backing arrangement comprising flex layers.

3. The printed circuit board (PCB) of claim 2, wherein the PCR chamber is contained within the flex layers.

4. The printed circuit board (PCB) of claim 3, wherein the flex layers are made of Kapton compatible with the PCR.

5. The printed circuit board (PCB) of claim 2, wherein a flame retardant 4 (FR-4) based construction is located beneath the flex layers, the FR-4 based construction containing electronic circuit board traces and a heater for heating the PCR chamber.

6. The printed circuit board (PCB) of claim 5, wherein the heater comprises a trace coil.

7. The printed circuit board (PCB) of claim 6, wherein the trace coil comprises copper.

8. The printed circuit board (PCB) of claim 5, wherein the electronic circuit board traces comprise a PCR temperature controller configured to control the heater.

9. The printed circuit board (PCB) of claim 8, further comprising a temperature sensing device connected to the temperature controller and associated with the PCR chamber such that the sensing device measures the temperature of the PCR chamber.

10. The printed circuit board (PCB) of claim 8, wherein the heater comprises a trace coil and the temperature sensing device comprises a sensitive resistance measurement circuit connected to the temperature controller and to the trace coil.

11. The printed circuit board (PCB) of claim 8, wherein the temperature controller comprises an anti-windup component.

12. The printed circuit board (PCB) of claim 8, wherein the temperature controller comprises a low pass filter.

13. The printed circuit board (PCB) of claim 8, wherein the temperature controller comprises an asymmetry correction unit.

14. The printed circuit board (PCB) of claim 8, wherein the temperature controller comprises an actuator-saturation correction unit.

* * * * *